(12) United States Patent
Oonuma

(10) Patent No.: US 8,703,055 B2
(45) Date of Patent: Apr. 22, 2014

(54) AUTOMATIC ANALYSIS APPARATUS AND DISPENSING METHOD FOR THE SAME

(75) Inventor: Takehiko Oonuma, Sakura (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1590 days.

(21) Appl. No.: 11/488,722

(22) Filed: Jul. 19, 2006

(65) Prior Publication Data

US 2007/0020145 A1 Jan. 25, 2007

(30) Foreign Application Priority Data

Jul. 21, 2005 (JP) ................................. 2005-210845

(51) Int. Cl.
*G01N 31/00* (2006.01)

(52) U.S. Cl.
USPC .......................................................... 422/64

(58) Field of Classification Search
USPC ........................................ 422/64, 72; 436/45
See application file for complete search history.

(56) References Cited

U.S. PATENT DOCUMENTS 5,677,188 A 10/1997 Mitsumaki et al.
6,409,968 B1 * 6/2002 Takahashi ....................... 422/64

FOREIGN PATENT DOCUMENTS

| EP | 0 316 766 A2 | 5/1989 |
| EP | 0 316 766 A3 | 5/1989 |
| EP | 1 422 528 A2 | 5/2004 |
| EP | 1 422 528 A3 | 5/2004 |
| EP | 1 460 432 A1 | 9/2004 |
| GB | 2 131 168 A | 6/1984 |
| JP | 63-180838 | 7/1988 |
| JP | 63-275957 | 11/1988 |
| JP | 3-140869 | 6/1991 |
| JP | 9-101313 | 4/1997 |
| WO | WO 03/012454 | 2/2003 |

* cited by examiner

*Primary Examiner* — Natalia Levkovich
(74) *Attorney, Agent, or Firm* — Oblon, Spivak, McClelland, Maier & Neustadt, L.L.P.

(57) ABSTRACT

An automatic analysis apparatus analyzing a test specimen held in a reaction vessel on the basis of a property of a mixed liquid of the test specimen and a reagent, includes a plurality of reaction vessels which corresponds to a plurality of measurement channels, respectively, a moving unit which moves the plurality of the reaction vessels then stops them at every analysis recycle, a control unit which controls the dispensing unit so as to aspirate the test specimen during movements of the reaction vessels, infuse the test specimen to one of the plurality of the reaction vessels after the reaction vessels stop, and repeatedly aspirate the test specimen and infuse the test specimen to one or more reaction vessels except the first reaction vessel among the plurality of the reaction vessels during stoppages of the reaction vessels.

8 Claims, 12 Drawing Sheets

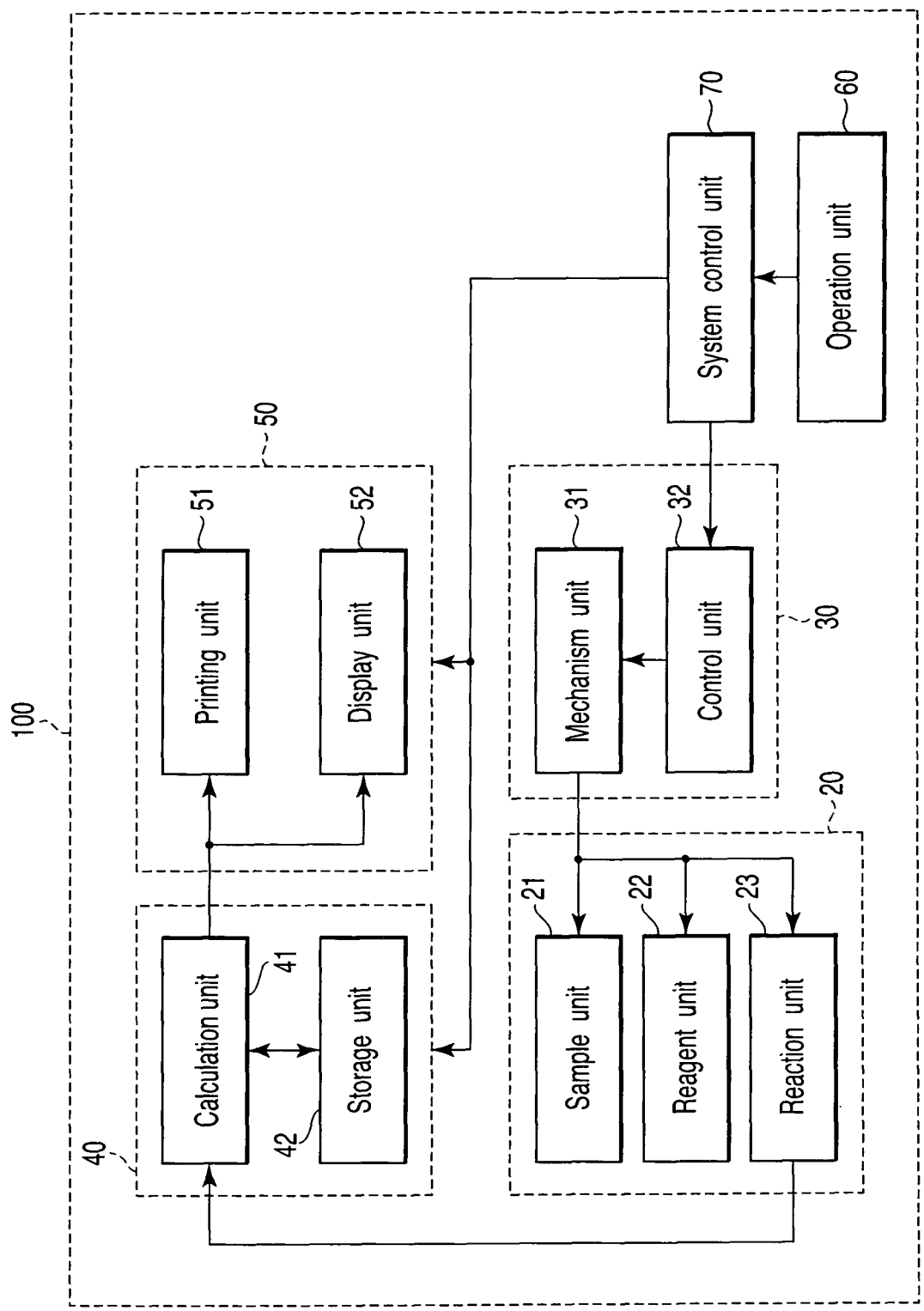
F I G. 1

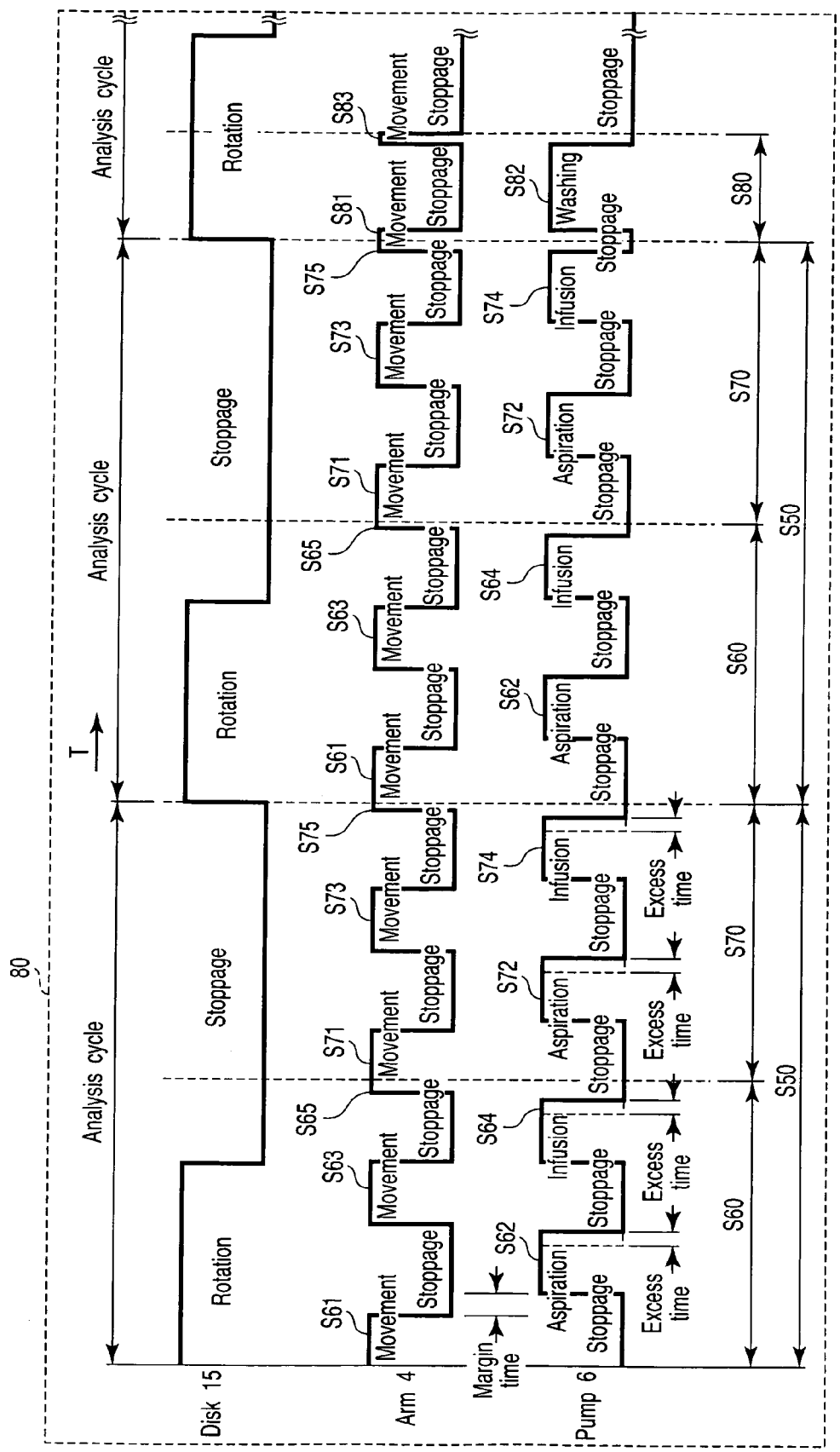
F I G. 5

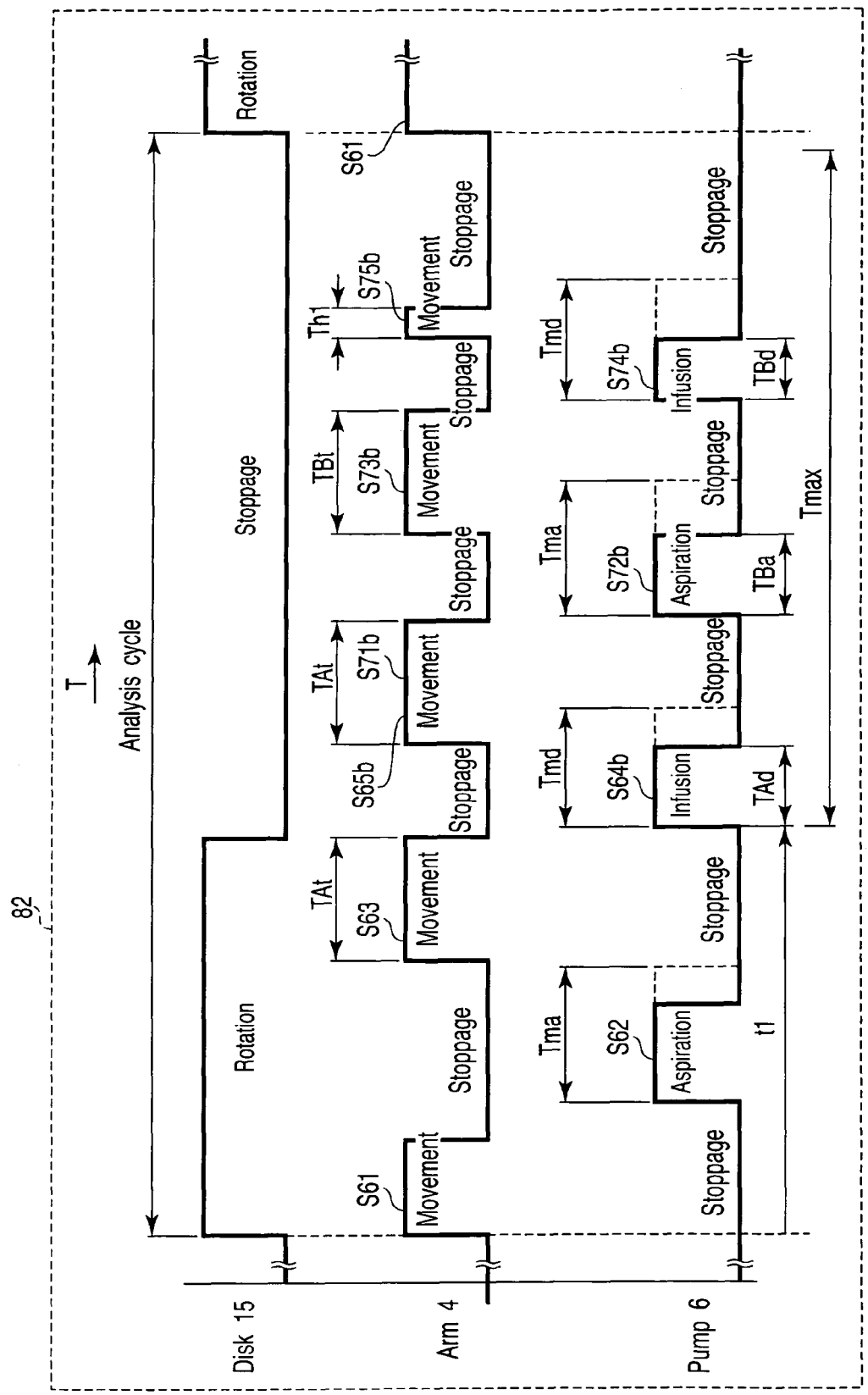
F I G. 10

AUTOMATIC ANALYSIS APPARATUS AND DISPENSING METHOD FOR THE SAME

CROSS-REFERENCE TO RELATED APPLICATIONS

This application is based upon and claims the benefit of priority from prior Japanese Patent Application No. 2005-210845, filed Jul. 21, 2005, the entire contents of which are incorporated herein by reference.

BACKGROUND OF THE INVENTION

1. Field of the Invention

The present invention is related to an automatic analysis apparatus and a dispensing method for the same analyzing components contained in a liquid.

2. Description of the Related Art

An automatic analysis apparatus measures a change in color or the like generated in a mixed liquid of a test specimen and a reagent by utilizing a transmission quantity of light, etc. The analysis apparatus analyzes densities of a variety of substances to be tested and activities of enzymes in the test specimen on the basis of the measurement result.

The analysis apparatus presets analysis conditions such as a quantity of the test specimen and the reagent, a reaction time of the mixed liquid or a wavelength of the light, etc., to be used for the measurement for each measurement item, and further selects to set measurement items to be measured for each test specimen before starting the measurement. The analysis apparatus measures the measurement items selected for each test specimen in relation to each of a large number of test specimens.

As for the measurement, a random access system and a semi-random access system have been well known. The semi-random access system can perform processing at a speed higher than that of the random access system. The semi-random access system is known, for instance, by Jpn. Pat. Appln. KOKAI Publication No. 9-101313.

In the random access system, the a specimen is dispensed from a specimen vessel into reaction vessels by using one probe corresponding to one measurement channel (also called measurement line) for each analysis cycle. Then, a reagent appropriate for the measurement item selectively set in advance is dispensed from the reagent vessel into the reaction vessels with the test specimen dispensed therein by using a reagent dispensing probe corresponding to the measurement channel.

The semi-random access system further includes a multiple item dispensing system and a single item dispensing system. The multiple item dispensing system aspirates the test specimen for a plurality of measurement channels at once by one probe. The multiple item dispensing system then divides the test specimen from the probe to infuse it to a plurality of reaction vessels each corresponding to the plurality of measurement channels. The single item dispensing system infuses the test specimen held in one specimen vessel at the same time by a plurality of probes each corresponding to the plurality of measurement channels. The single item dispensing system then infuses the test specimen from the plurality of probes to the plurality of reaction vessels each corresponding to the plurality of measurement channels, respectively.

By the way, the automatic analysis apparatus aspirates the test specimen to the probe and infuses the test specimen therefrom by aspirating and infusing a pressure transferring medium such as water sealed in a tube through the probe and a pump connected by the tube. The test specimen aspirated by the probe is sometimes contacted with the pressure transferring medium and diluted by the transferring medium near by the contact point. Therefore, the analysis apparatus is so constituted as not to infuse the test specimen diluted by the transferring medium to the reaction vessels by aspirating the test specimen of a volume larger than that of infusing to the reaction vessels. The test specimen aspirated by the probe but not infused to the reaction vessels is called a dummy.

In the multiple item dispensing system, since a large volume of test specimen is aspirated in the probe at once and a plurality of times of infusion operations are repeated, a mixture of the test specimen and the pressure transferring medium is apt to be caused in the probe, and there is a risk that even the test specimen infused to the reaction vessels is diluted by the transferring medium. Therefore there is a risk of a reduction in precision, for instance, in analyzing an immunity item of an extremely low density, so that the single item dispensing system is preferable for achieving an analysis with high precision.

However, in the single item dispensing system, the probe and pump, etc., of the same number as that of the measurement channels being required, an automatic analysis apparatus results in becoming complex and expensive.

BRIEF SUMMARY OF THE INVENTION

In these circumstances, an automatic analysis apparatus capable of accurately dispensing a test specimen even simple in configuration has been desired.

According to a first aspect of the present invention, there is provided an automatic analysis apparatus analyzing a test specimen held in a reaction vessel on the basis of a property of a mixed liquid of the test specimen and a reagent, comprising: a plurality of reaction vessels which corresponds to a plurality of measurement channels, respectively; a moving unit which moves the plurality of the reaction vessels then stops them at every analysis recycle; a control unit which controls the dispensing unit so as to aspirate the test specimen during movements of the reaction vessels, infuse the test specimen to one of the plurality of the reaction vessels after the reaction vessels stop, and repeatedly aspirate the test specimen and infuse the test specimen to one or more reaction vessels except the first reaction vessel among the plurality of the reaction vessels during stoppages of the reaction vessels.

According to a second aspect of the present invention, there is provided an automatic analysis apparatus analyzing a test specimen held in a reaction vessel on the basis of a property of a mixed liquid of the test specimen and a reagent, comprising: a plurality of reaction vessels which corresponds to a plurality of measurement channels, respectively; a first moving unit which moves the plurality of the reaction vessels then stops them at every analysis recycle; a aspirating/infusing unit which aspirates the test specimen from a specimen vessel by a dispensing probe to infuse the test specimen; a second moving unit which moves the dispensing probe; and a control unit which controls the aspirating/infusing unit so as to aspirate from the test specimen during movements of the plurality of the reaction vessels, and then, during the plurality of the reaction vessels stop after stopping them, (i) controls the second moving unit so as to move the dispensing probe into a first reaction vessel among the plurality of the reaction vessels, (ii) controls the aspirating/infusing unit so as to infuse the test specimen into the specimen vessel, (iii) controls the second moving unit so as to move the dispensing probe to the specimen vessel, and (iv) controls the aspirating/infusing unit and the second moving unit so as to repeatedly aspirate the test specimen and infuse the test specimen to one or more reaction vessels except the first reaction vessel among the plurality of the reaction vessels.

According to a third aspect of the present invention, there is provided a dispensing method of dispensing a test specimen in a automatic analysis apparatus comprising: a plurality of reaction vessels which corresponds to a plurality of measurement channels, respectively; a moving unit which moves the plurality of the reaction vessels then stops them at every analysis recycle; and a dispensing unit which aspirates the test specimen from a specimen vessel to infuse the test specimen to a first reaction vessel among the plurality of the reaction vessels stopped by the moving unit, the dispensing method comprising: aspirating the test specimen during movements of the reaction vessels by the dispensing unit, infusing the test specimen to one of the plurality of the reaction vessels by the dispensing unit after the reaction vessels stop, and repeatedly aspirating the test specimen and infusing the test specimen to one or more reaction vessels except the first reaction vessel among the plurality of the reaction vessels by the dispensing unit during stoppages of the reaction vessels.

According to a fourth aspect of the present invention, there is provided a dispensing method of dispensing a test specimen in a automatic analysis apparatus comprising: a plurality of reaction vessels which corresponds to a plurality of measurement channels, respectively; a first moving unit which moves the plurality of the reaction vessels then stops them at every analysis recycle; a aspirating/infusing unit which aspirates the test specimen from a specimen vessel by a dispensing probe to infuse the test specimen; and a second moving unit which moves the dispensing probe, the dispensing method comprising: aspirating the test specimen during movements of the plurality of the reaction vessels, and then, during the plurality of the reaction vessels stop after stopping them, (i) moving the dispensing probe into a first reaction vessel among the plurality of the reaction vessels by the second moving unit, (ii) infusing the test specimen into the specimen vessel by the aspirating/infusing unit, (iii) moving the dispensing probe to the specimen vessel by the second moving unit, and (iv) repeatedly aspirating the test specimen and infusing the test specimen to one or more reaction vessels except the first reaction vessel among the plurality of the reaction vessels by the aspirating/infusing unit and the second moving unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a view showing a configuration of an automatic analysis apparatus regarding a first embodiment of the present invention;

FIG. 5 is a flowchart showing operation timing of each step in the sample dispensing process and the probe washing process shown in FIG. 4;

FIG. 10 is a timing chart showing timing of operations of each step of a sample dispensing process regarding a third embodiment of the present invention;

DETAILED DESCRIPTION OF THE INVENTION

Figure 2:
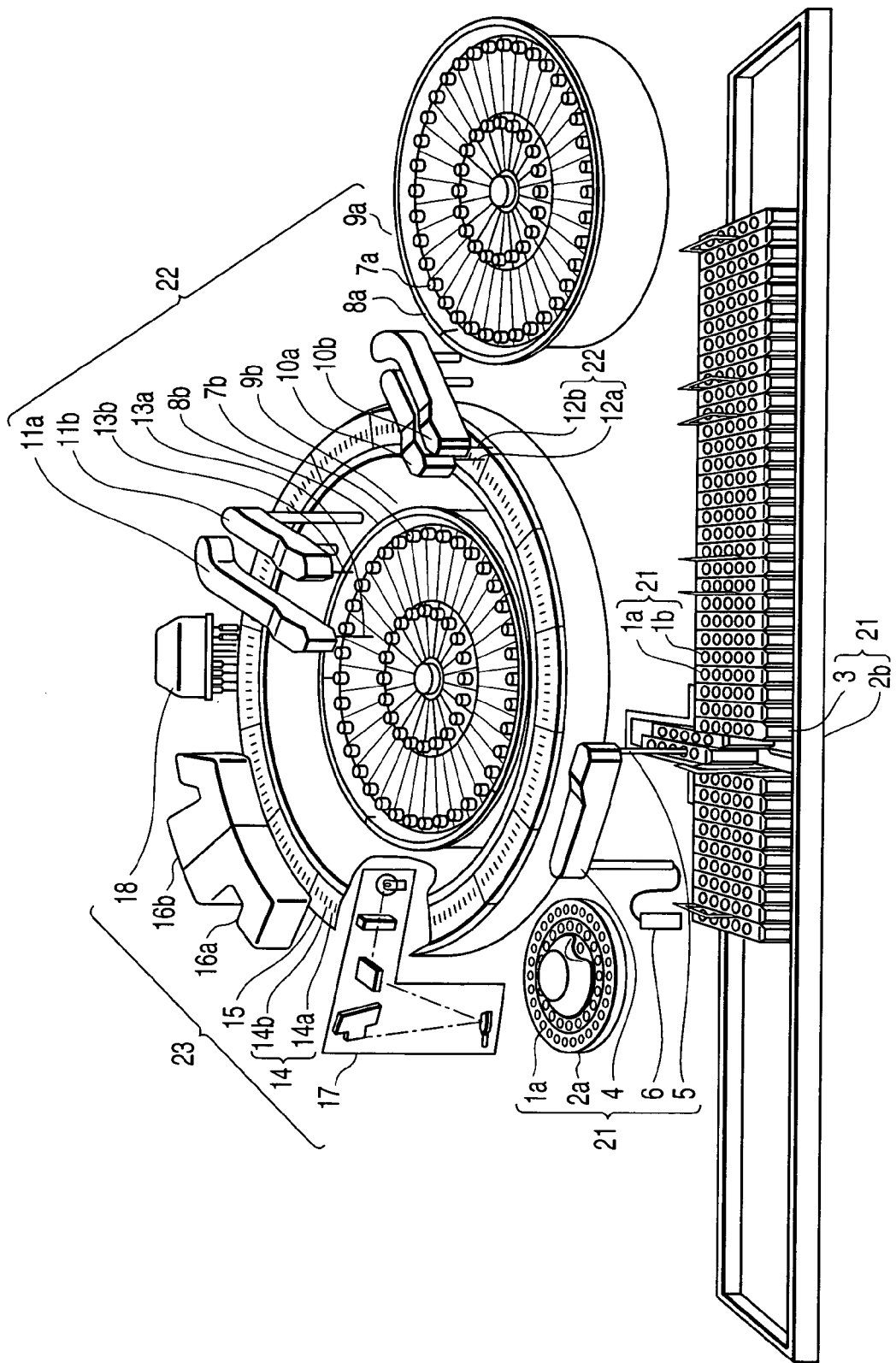
FIG. 2 is a perspective view showing a configuration of an analysis unit in FIG. 1.

Hereinafter, embodiments of the present invention will be described with reference to the drawings.

First Embodiment

FIG. 1 is a block diagram showing a configuration of an automatic analysis apparatus 100 regarding a first embodiment of the present invention. The analysis apparatus 100 adopts a semi-random access system and includes a first and a second measurement channels installed so as to enable measuring two measurement items.

The analysis apparatus 100 includes, as shown in FIG. 1, a measuring unit 20, an analysis control unit 30, an analysis data processing unit 40, an output unit 50, an operation unit 60 and a system control unit 70.

The measuring unit 20 further includes a sample unit 21, a reagent unit 22 and a reaction unit 23. The sample unit 21 manages a calibrator for each measurement item and a sample of a test specimen extracted from a patient. The reagent unit 22 manages reagents to be chemically reacted with components of a sample corresponding to the measurement items. The reaction unit 23 performs a measurement corresponding to the measurement items in relation to the mixed liquid of the sample and the reagent. The reaction unit 23 outputs a calibrator signal and an analysis signal showing the measurement results of the calibrator and the test specimen, respectively, to the data processing unit 40.

The control unit 30 further includes a mechanical unit 31 and a control unit 32. The mechanical unit 31 drives a variety of movable elements described bellow included in the measuring unit 20. The control unit 32 controls an operation of the mechanical unit 31.

The data processing unit 40 further includes a calculation unit 41 and a storage unit 42. The calculation unit 41 creates a calibration table for each measurement item on the basis of the calibrator signal output from the measuring unit 20. The calculation unit 41 calculates analysis data for each measurement item, based on the analysis signal and the calibration table output from the measuring unit 20. The storage unit 42 has a hard disk, etc. to store the calibration table, the analysis data and the like. The calculation unit 41 outputs the calibration table and the analysis data to the output unit 50 if necessary.

The output unit 50 further includes a printing unit 51 and a display unit 52. The printing unit 51 has a printer, etc. to print the calibration table and the analysis data output from the calculation unit 41 in a prescribed format on a printer paper or the like. The display unit 52 has a cathode-ray tube (CRT) and a liquid crystal display (LCD), etc. to display the calibration table and the analysis data output from the calculation unit 41. The display unit 52 displays a patient information inputting screen to input an ID and a name of a patient, an analysis condition setting screen to set analysis conditions for each measurement item, a measurement item setting screen to selectively set measurement items for each test specimen, etc. under control by the system control unit 70.

The operation unit 60 has input devices such as a keyboard, a mouse, a button, and a touch key panel. The operation unit 60 is operated by an operator to set the analysis conditions for each measurement item, to input patient information such as the ID and the name of the patient, to selectively input the measurement items for each test specimen, to calibrate each measurement item, to measure the test specimen, and the like. The operation unit 60 outputs a command signal indicating contents of operations by the operator to the system control unit 70.

The system control unit 70 has a CPU and a storage circuit and integrally controls each unit of the automatic analysis apparatus 100. Specifically, the system control unit 70 determines the analysis conditions of the measurement items, the patient information, and the measurement items for each test specimen, etc on the basis of the command signal supplied from the operation unit 60 to store such information. The system control unit 70 controls the operations of the measuring unit 20 so as to measure in a prescribed sequence in a fixed cycle, based on the information. The system control unit 70 controls the data processing unit 40 on order to create a necessary calibration table and calculate necessary analysis data. The system control unit 70 further controls the output unit 50 so as to output the calibration table and the analysis data in a required form.

FIG. 2 is a perspective view showing a configuration of the sample unit 21, the reagent unit 22 and the reaction unit 23.

The sample unit 21 includes specimen vessels 1a, 1b, samplers 2a, 2b, a rack 3, an arm 4, a dispensing probe 5 and a pump 6.

The specimen vessels 1a, 1b holds a calibrator, a specimen for precision management, or a sample such as a test specimen. The specimen vessel 1b holds a small quantity of a test specimen extracted form a child so as to enabling it to be aspirated. That is, the specimen vessel 1b can be made so that its horizontal cross section is smaller than that of the specimen vessel 1a and the water surface of a small quantity of a test specimen stored in the specimen vessel 1b becomes higher than that of the specimen vessel 1a.

The sampler 2a can set a large number of specimen vessels 1a by arranging at two rows circumferentially. The sampler 2a moves the set specimen vessels 1a along with the circumference by rotating itself. Each position at which the specimen vessels 1a are set in the sampler 2a is assigned to setting positions for the calibrator or for the specimen for the precision management in advance. The specimen vessels 1a with the calibrators each held therein are set at the former setting positions, and the specimen vessels 1a with specimens for the precision management held therein are set at the latter setting positions.

The sampler 2b can set a large number of racks 3. The racks 3 can be set by arranging a plurality of specimen vessels 1a and 1b in straight lines. The racks 3 are arranged along with directions perpendicular to the arrangement directions of the specimen vessels 1a and 1b. The sampler 2b moves the racks in their arrangement directions. The sampler 2b moves the racks 3 in those arrangement directions. The sampler 2b also moves the racks 3 in directions perpendicular to their arrangement directions at positions at which the sampler 2b extracts the sample. Each position at which the specimen vessels 1a and 1b are set in each rack 3 are assigned to the setting positions of the test specimens in advance, the specimen vessels 1a and 1b with the test specimens each held therein are set at those setting positions.

The arm 4 is supported at its one end rotatably. The dispensing probe 5 is attached to the other end of the arm 4. The arm 4 supports the dispensing probe 5 in a vertical direction so as to enable it to be moved. Thus, the arm 4 moves the dispensing probe 5 along with an arc-like trace and moves it up and down.

The dispensing probe 5 has a slim cavity inside thereof and the pump 6 is connected to the cavity though the arm 4. The dispensing probe 5 extracts the sample by making an inside of the cavity put negative pressure by the pump 6. And the dispensing probe 5 infuses the sample in a manner in which the negative pressure in the cavity is eliminated by the pump 6. A sensor to detect a liquid surface of the sample is disposed at the tip end of the dispensing probe 5 and the sensor detects the liquid surface when the tip end of the dispensing probe 5 is inserted up to a prescribed depth, for instance, about 2 mm from the liquid surface of the sample.

The pump 6 brings the inside of the cavity of the dispensing probe 5 into the negative pressure by aspirating the pressure transferring medium such as water to eliminate the negative pressure inside the cavity of the dispensing probe 5.

The reagent unit 22 includes reagent bottles 7a and 7b, reagent racks 8a and 8b, reagent storage 9a and 9b, arms 10a, 10b, 11a and 11b, and dispensing probes 12a, 12b, 13a and 13b.

The reagent bottle 7a holds a first reagent selectively reacting to a sample. The reagent bottle 7b holds the first reagent and a second reagent.

The reagent racks 8a and 8b holds the reagent bottles 7a and 7b, respectively.

The reagent storages 9a and 9b rotatably hold the reagent racks 8a and 8b, respectively.

The arms 10a, 10b, 11a and 11b are so supported at their one ends as to become rotatable, respectively. The dispensing probes 12a, 12b, 13a and 13b are attached to the other ends of the arms 10a, 10b, 11a and 11b, respectively. The arms 10a, 10b, 11a and 11b support the dispensing probes 12a, 12b, 13a and 13b so that they become vertically movable, respectively. Thus, the arms 10a, 10b, 11a and 11b moves the dispensing probes 12a, 12b, 13a and 13b along with arc-like traces and moves them up and down, respectively.

The dispensing probes 12a, 12b, 13a and 13b each have slim cavities inside and connected to pumps (not shown) through the arms 10a, 10b, 11a and 11b, respectively. The dispensing probes 12a, 12b, 13a and 13b each aspirate and infuse the reagents as like the dispensing probe 5.

The reaction unit 23 includes a reaction vessel group 14, a disk 15, stirring units 16a and 16b, a photometry unit 17 and a washing unit 18.

The reaction vessel group 14 is formed by arranging a plurality of reaction vessels 14a and 14b assigned respectively to a first and a second measurement channels alternately and circumferentially. The reaction vessels 14a and 14b each holds mixed liquids of the sample and the reagent.

The disk 15 holds the reaction vessel group 14 rotatably. The disk 15 rotates counter-clockwise, for instance, by an angle to which an angle corresponding to each reaction vessel 14a and 14b is added to 360° for four analysis cycles. One analysis cycle is, for instance, 4.5 sec. The disk 15 may be rotated clockwise. The disk 15 may be rotated by an angle from which an angle corresponding to each reaction vessel 14a and 14b is subtracted from 360° for the four analysis cycles.

The stirring unit 16a has two stirring elements. The stirring unit 16a can move the two stirring elements above the reaction vessels 14a and 14b between the corresponding two stirring positions and two washing positions differing therefrom. The stirring unit 16a can move the two stirring elements vertically. The stirring unit 16a has a function to wash the two stirring elements at two washing positions, respectively. The stirring unit 16a is used for stirring the sample dispensed into the reaction vessels 14a and 14b and the first reagent.

The stirring unit 16b has two stirring elements. The stirring unit 16b can move the two stirring elements above the reaction vessels 14a and 14b between the corresponding two stirring positions and two washing positions differing therefrom, respectively. The stirring unit 16b can move the two stirring elements vertically. The stirring unit 16b has a function capable of each washing the two stirring elements at the two washing positions, respectively. The stirring unit 16b is used for stirring the samples dispensed in the reaction vessels 14a and 14b and the first and the second reagents.

The photometry unit 17 emits light when the reaction vessels 14a and 14b pass through photometry positions to measure absorbency of set wavelengths from the transmitted light. The photometry unit 17 generates an analysis signal as a signal indicating the measured absorbency.

The washing unit 18 has a washing nozzle and a drying nozzle. The washing unit 18 aspirates and washes the mixed liquids in the reaction vessels 14a and 14b through the washing nozzle. The washing unit 18 dries the insides of the reaction vessels 14a, 14b. The reaction vessels 14a and 14b washed and dried by the washing unit 18 are used for measurement again.

Figure 3:
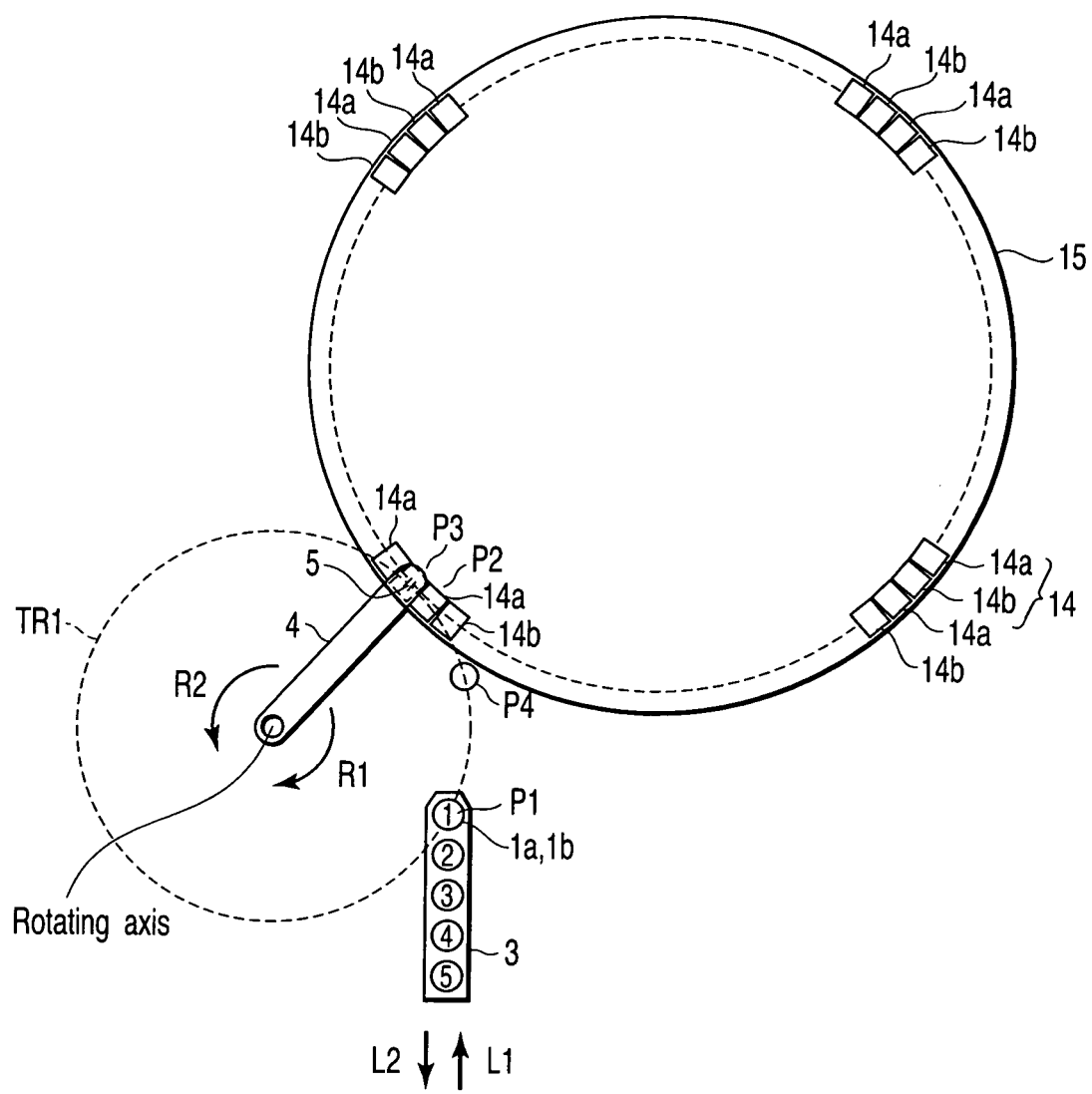
FIG. 3 is a view of a part of a sample unit and a reaction unit in FIG. 2 viewed from above.

FIG. 3 is a view of a part of the sample unit 21 and the reaction unit 23 viewed from above.

The arm 4 rotates in a direction of an arrow R1 or an arrow R2 with its one end as a rotating axis. With the rotation of the arm 4, the dispensing probe 5 moves along a trace TR1 indicated by a dot line.

A aspiration position P1, a first and a second infusion positions P2 and P3, and a washing position P4 are set on the trace TR1. The aspiration position P1 is positioned near by the first and the second infusion positions P2 and P3. The washing position P4 is positioned between the aspiration position P1 and the first and the second infusion positions P2 and P3. The dispensing probe 5 can move in a short time between the aspiration position P1 and the first and the second infusion positions P2 and P3, and between the first and the second infusion positions P2 and P3 and the washing position P4, and between the washing position P4 and the aspiration position P1.

The movement of the rack 3 in an arrow L1 and an arrow L2 directions makes arbitrary specimen vessels 1a and 1b stop blow the aspiration position P1. At the aspiration position P1, the dispensing probe 5 aspirates the samples held in the specimen vessels 1a and 1b stopped blow the aspiration position P1.

With the disk 5 rotated, arbitrary reaction vessels 14a and 14b stop below the first and the second infusion positions P2 and P3, respectively. At the first infusion position P2, the dispensing probe 5 infuses the sample to the reaction vessel 14a stopped blow the first infusion position P2. At the second infusion position P3, the dispensing probe 5 infuses the sample to the reaction vessel 14b stopped below the second infusion position P3. The dispensing probe 5 is washed at the washing position P4. In other words, the dispensing probe 5 is commonly used for both first and second measurement channels.

The mechanical unit 31 includes a plurality of mechanisms. Some of the mechanisms rotate the sampler 2a, the arms 4, 10a, 10b, 11a and 11b, the reagent storages 9a and 9b, two stirring elements of the stirring unit 16a, and two stirring elements of the stirring unit 16b, respectively. Some of the mechanisms moves the arms 4, 10a, 10b, 11a and 11b, the reagent storages 9a and 9b, two stirring elements of the stirring unit 16a, and two stirring elements of the stirring unit 16b, and the washing unit 18 up and down, respectively. Some of the mechanisms drive the pump 6 and pumps to aspirate/infuse reagents in the dispensing probes 12a, 12b, 13a and 13b, respectively. Some of the mechanisms make the two stirring elements of the stirring unit 16a and the two stirring elements of the stirring unit 16b perform stirring operations, respectively. One of the mechanisms drives a washing pump infusing and aspirating the washing liquid from the washing nozzle of the washing unit 18. One of the mechanisms drives a drying pump aspirating the washing liquid from the drying nozzle of the washing unit 18.

The control unit 32 includes a control circuit to each control each mechanism included in the mechanism unit 31, respectively. The control unit 32 operates each mechanism of the mechanism unit 31 in analysis cycle.

Next to this, operations to dispense the test specimen into the reaction vessels 4a and 4b will be described in detail.

Figure 4:
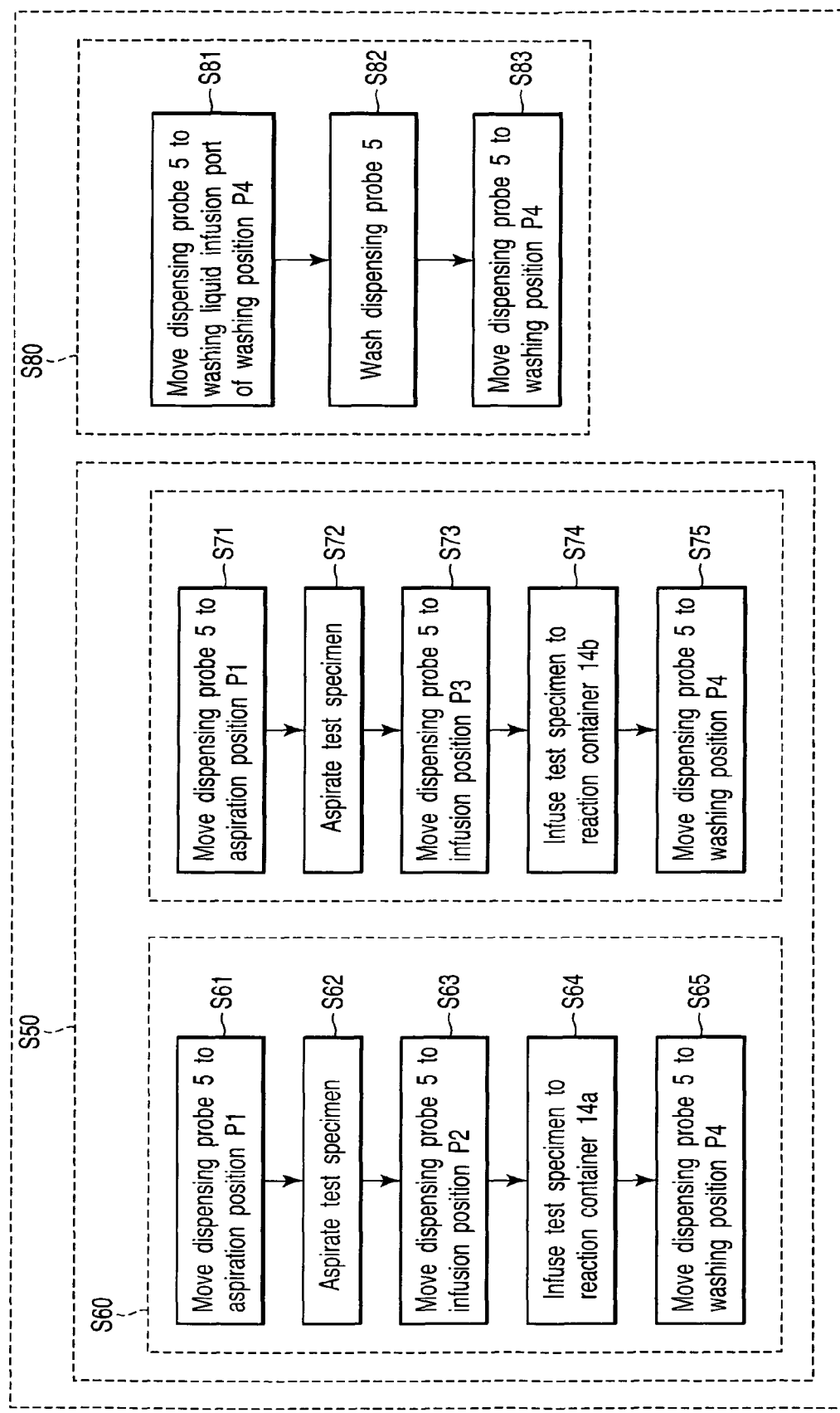
FIG. 4 is a flowchart showing a sample dispensing process and a probe washing process in the analysis apparatus shown in FIG. 1.

FIG. 4 is a flowchart showing a sample dispensing process S50 and a probe washing process S80.

The sample dispensing process S50 is a process to dispense the test specimen into the reaction vessels 4a and 4b. The probe washing process S80 is a process follows the sample dispensing process S50.

The sample dispensing process S50 includes a first process S60 and a second process S70. The first process S60 is a process to dispense a test specimen in relation to a first measurement channel. The second process S70 is a process to dispense a test specimen in relation to a second measurement channel. Usually, although the sample dispensing process S50 is executed at every analysis cycle, only the first process S60 or the second process S70 may be executed for one analysis cycle.

The control unit 32 executes the sample dispensing process S50 on the basis of an instruction for a measurement from the system control unit 70.

The first process S60 includes of steps S61 to S65.

In the step S61, during the rotation of the disk 15, the control unit 32 rotates the arm 4 in the arrow R1 direction in FIG. 3 to move the dispensing probe 5 from the washing position P4 to the aspiration position P1. The control unit 32 further lowers the arm 4 until the tip end of the dispensing probe 5 detects the liquid surface of the test specimen in the specimen vessels 1a or 1b. The control unit 32 moves the rack 3 by the sampler 2b and positions either the specimen vessels 1a or 1b with the test specimen to be aspirated held therein at the position below the aspiration position P1.

In the step S62, the control unit 32 makes the pump 6 perform a aspiration operation and makes the dispensing probe 5 aspirate the test specimen from the specimen vessel 1a or the specimen vessel 1b.

In the step S63, the control unit 32 rises the arm 4, rotates the arm 4 in the arrow R2 direction in FIG. 3 then moves the dispensing probe 5 to the first infusion position P2. After stopping the rotation of the disk 15, the control unit 32 further lowers the arm 4 to a prescribed position at which the tip end of the dispensing probe 5 arrives inside the reaction vessel 14a.

In the step S64, the control unit 32 makes the pump 6 perform a infusion operation to make the reaction vessel 14a stopped below the first infusion position P2 infuse the test specimen.

In the step S65, the control unit 32 rises the arm 4, rotates the arm 4 in the arrow direction R1 in FIG. 3 then moves the dispensing probe 5 to the washing position. P4.

The second process S70 includes of steps S71 to S75.

In the step S71, the control unit 32 rotates the arm 4 in the arrow R1 direction in FIG. 3 during the rotation of the disk 15 to move the dispensing probe 5 from the washing position P4 to the aspiration position P1. The control unit 32 further lowers the arm 4 until the tip end of the dispensing probe 5 detects the liquid surface of the test specimen in the specimen vessel 1a or 1b.

In the step S72, the control unit 32 makes the pump 6 perform a aspiration operation and makes the dispensing probe 5 aspirate the test specimen from the specimen vessel 1a or 1b.

In the step S73, the control unit 32 rises the arm 4, rotates the arm 4 in the arrow R2 direction in FIG. 3 then moves the dispensing probe 5 to the second infusion position P3. The control unit 32 further lowers the arm 4 to a prescribed position at which the tip end of the dispensing probe 5 arrives in the reaction vessel 14b after the rotation of the disk 15 stops.

In the step S74, the control unit 32 makes the pump 6 perform a infusion operation and makes the dispensing probe 5 infuse the test specimen to the reaction vessel 14b stopped below the second infusion position P3.

In step S75, the control unit 32 rises the arm 4, rotates the arm 4 in the arrow R1 direction in FIG. 3 then moves the dispensing probe 5 to the washing position P4.

In the next analysis cycle after completing the sample dispensing process S50 for the last measurement item related to the same test specimen, the control unit 32 executes the probe washing process S80.

The probe washing process 80 is composed of steps S81 to S83.

In the step S81, the control unit 32 lowers the arm 4 until the tip end of the dispensing probe 5 achieves a infusion port for the washing liquid disposed at the washing position P4.

In the step S82, the control unit 32 operates the pump 6, and infuses the washing liquid from other flow path supplied through a switching valve disposed in a flow path for a pressure transferring medium between the pump 6 and the dispensing probe 5 to wash the inner wall of the dispensing probe 5. At this moment, infusing the washing liquid from the infusion port disposed near the washing position P4 causes washing the outer wall of the dispensing probe 5.

In step S83, the control unit 32 rises the arm 4 to standby it for the next dispensing of a test specimen.

FIG. 5 is a timing chart 80 showing operation timing of each step in the sample dispensing process S50 and the probe washing process S80.

The timing chart 80 shows each operation start timing, operation times and operation termination timing of the disk 15, the arm 4 and the pump 6 corresponding to the steps S61 to S65 in the first process S60, the steps S71 to S75 in the second process S70, and steps S81 to S83, respectively. An arrow T indicates an elapse direction of a time.

At first, detailed timing of operations of each step corresponding to the sample dispensing process S50 will be explained.

The sample dispensing process S50 is executed once per one analysis cycle. Therefore, the arm 4 sequentially moves under each control of the steps S61, S63, S71, S73 and S75 within a period of the one analysis cycle with stop periods intervened, respectively. The pump 6 sequentially performs the aspiration operation under control in the step S62, the infusion operation under control in the step S64, the aspiration operation under control in the step S72 and the infusion operation under control in the step S74 with the stop periods intervened, respectively. The disk 15 starts its rotation at the same time of the start of the analysis cycle and stops the rotation before the analysis cycle terminates after rotating by the forgoing fixed angel.

The movements under the control in the steps S61 and S71 include a rotation to move the dispensing probe 5 from the washing position P4 to the aspiration position P1 and a lowering operation to move the dispensing probe 5 up to the liquid surface detecting position of the test specimen.

The movement under the control of the step S63 includes the rising operation to move the dispensing probe 5 to the outsides of the specimen vessels 4a and 4b, the rotation to move the dispensing probe 5 from the aspiration position P1 to the first infusion position P2 and the lowering operation to move the dispensing probe 5 to the infusion position in the reaction vessel 14a.

The movement under the control of the step S65 includes the rising operation to move the dispensing probe 5 to the outside of the reaction vessel 14a and the rotation to move the dispensing probe 5 from the first infusion position P2 to the washing position P4.

The movement under the control of the step S71 includes the rotation to move the dispensing probe 5 from the washing position P4 to the aspiration position P1 and the lowering operation to move the dispensing probe 5 up to the liquid surface detecting position of the test specimen.

The movement under the control of the step S73 includes the rising operation to move the dispensing probe 5 to the outside of the specimen vessels 4a and 4b, the rotation to move the dispensing probe 5 from the first infusion position P1 to the second infusion position P3, and the lowering operation to move the dispensing probe 5 to the infusion position in the reaction vessel 14b.

The movement under the control in the step S75 includes the rising operation to move the dispensing probe 5 to the outside of the reaction vessel 14b and the rotation to move the dispensing probe 5 from the second infusion position P3 to the washing position P4.

The timing of the lowering operation of the arm 4 under the control of the step S63 is set in matching with the timing of the stop of the disk 15 so as to prevent the dispensing probe 5 from colliding with the reaction vessels 14a and 14b in rotations. The timing of the aspiration operation under the control in the step S62 is set in matching with the timing of the movement of the arm 4 under the control in the step S63. Thereby, a quantity of margin times is generated before starting the aspiration operation under the control in the step S62 after stopping the movement of the arm 4 under the control in the step S61.

In contrast, in the timing of the lowering operation of the arm 4 under the control in the step S73, it is not necessary to set the timing with stop timing of the disk 15 in mind, and there is no need of the margin time until the aspiration operation will be started under the control in the step S72 after stopping the movement of the arm 4 under the control in the step S71. As a result, the first process S60 needs a time longer than that of the second process S70.

A quantity of the test specimen (sample quantity) to be dispensed into either of the reaction vessel 14*a* or 14*b* is set as analysis conditions for each measurement item. The control unit 32 changes the time period of the aspiration operation and the infusion operation of one time by the pump 6 in response to the set sample quantity. The time periods of the aspiration operation and the infusion operation shown in FIG. 5 indicate ones necessary for the case in which the sample quantity is set to a maximum quantity. Therefore, in the event where the sample quantity is set smaller than the maximum quantity, the time periods of the aspiration operation and the infusion operation become shorter than those shown in FIG. 5. On the other hand, since the timing at which the aspiration operation and the infusion operation of the pump 6 are not changed, in the event where the sample quantity is set to a quantity smaller than the maximum quantity, a excess time occurs after starting the aspiration and infusion operations of the pump 6 until the next movement of the arm 4 is started. For instance, FIG. 5 shows, by dot lines, an example of the step timing of the aspiration and infusion operations of the pump 6 in the case in which the sample quantity is set smaller than the maximum quantity. During the time period corresponding to the excess time, the arm 4 and the pump 6 each maintain the unchanged states.

The rotation and the up-down operation of the arm 4 under the control of each step initially accelerate the dispensing probe 5, then move it at a constant high-speed and further reduce the speed and stop it. However, the rotation of the arm 4 to move the dispensing probe 5 from the second infusion position P3 to the washing position P4 under the control in the steps S65 and S75 and the rotation of the arm 4 to move the dispensing probe 5 from the washing position P4 to the aspiration position P1 under the control in the steps S71 and S61 are performed successively.

Next to this, timing of each step corresponding to the probe washing process S80 will be described in detail.

The probe washing process S80 is conducted once in the next analysis cycle after completing the sample dispensing process S50 to perform the last measurement item related to the same test specimen. Therefore, the arm 4 sequentially moves under each control in the steps S81 and S83 within the period of the one analysis cycle with the stop periods intervened, respectively. The pump 6 performs the washing operation under the control in the step S82.

The movement under the control in the step S81 is the lowering operation to move the dispensing probe 5 to the washing liquid infusion port.

The washing operation under the control in the step S82 is the infusion operation to infuse the washing liquid.

The movement under the control in the step S83 is the rising operation to move the dispensing probe 5 from the washing liquid infusion port to a position where it was.

Some test specimens includes, for example, an immunity item with an extremely low density apt to be affected from other test specimens. In the probe washing process S80 before dispensing the test specimen related to the measurement item preset as such item apt to be affected, the control unit 32 sets the time period to make the pump 6 perform the washing operation longer than usual one in the step S82.

Successively, operations of the automatic analysis apparatus 100 will be described.

Figure 6:
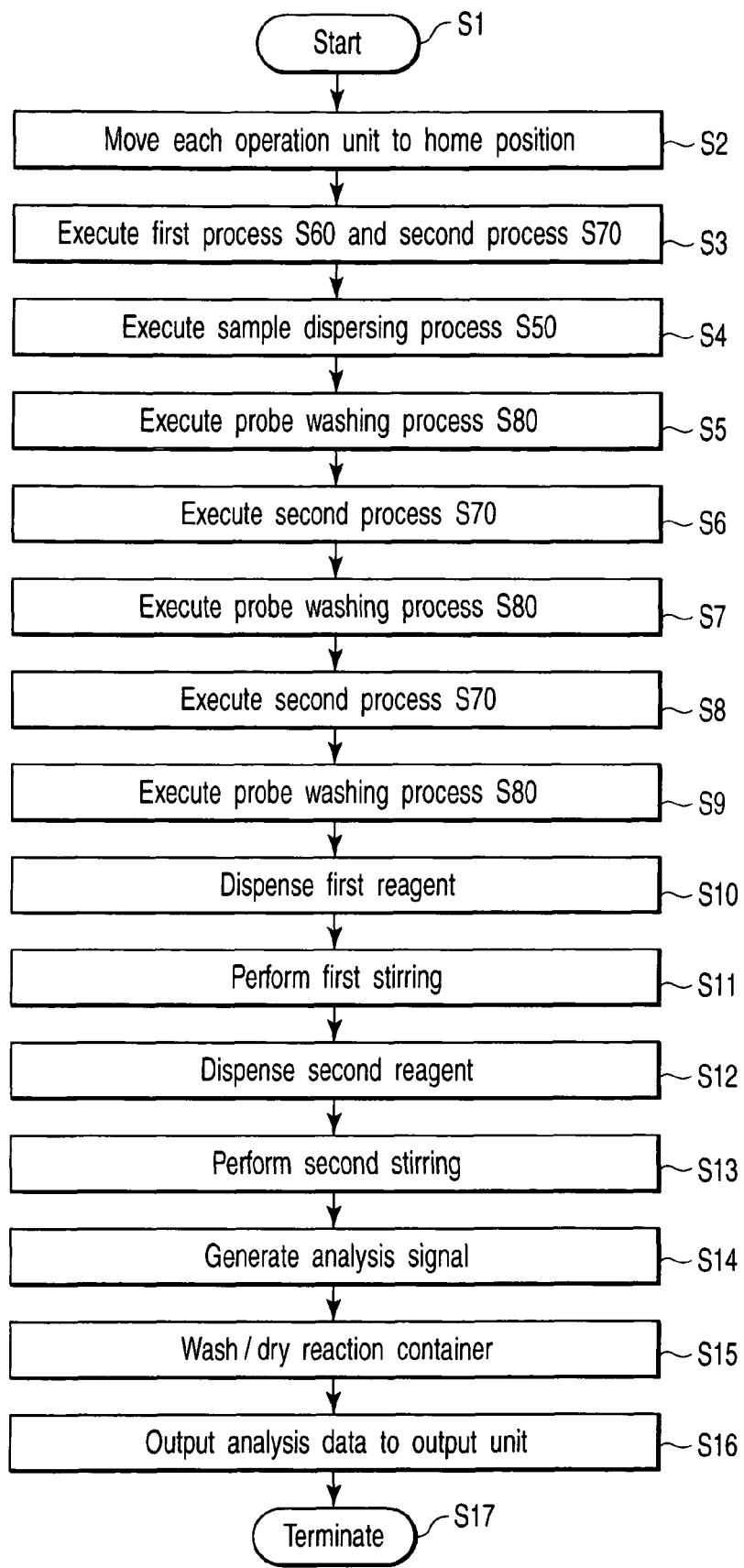
FIG. 6 is a flowchart showing an example of operations of the analysis apparatus shown in FIG. 1.

FIG. 6 is a flowchart showing an example of operations of the automatic analysis apparatus 100.

The storage unit 42 stores a calibration table of each measurement item created on the basis of a calibration operation by the operation unit 60. The internal storage circuit of the system control unit 70 stores the measurement items for each test specimen, based on the selecting operation for the measurement items by the operation unit 60.

Figure 7:
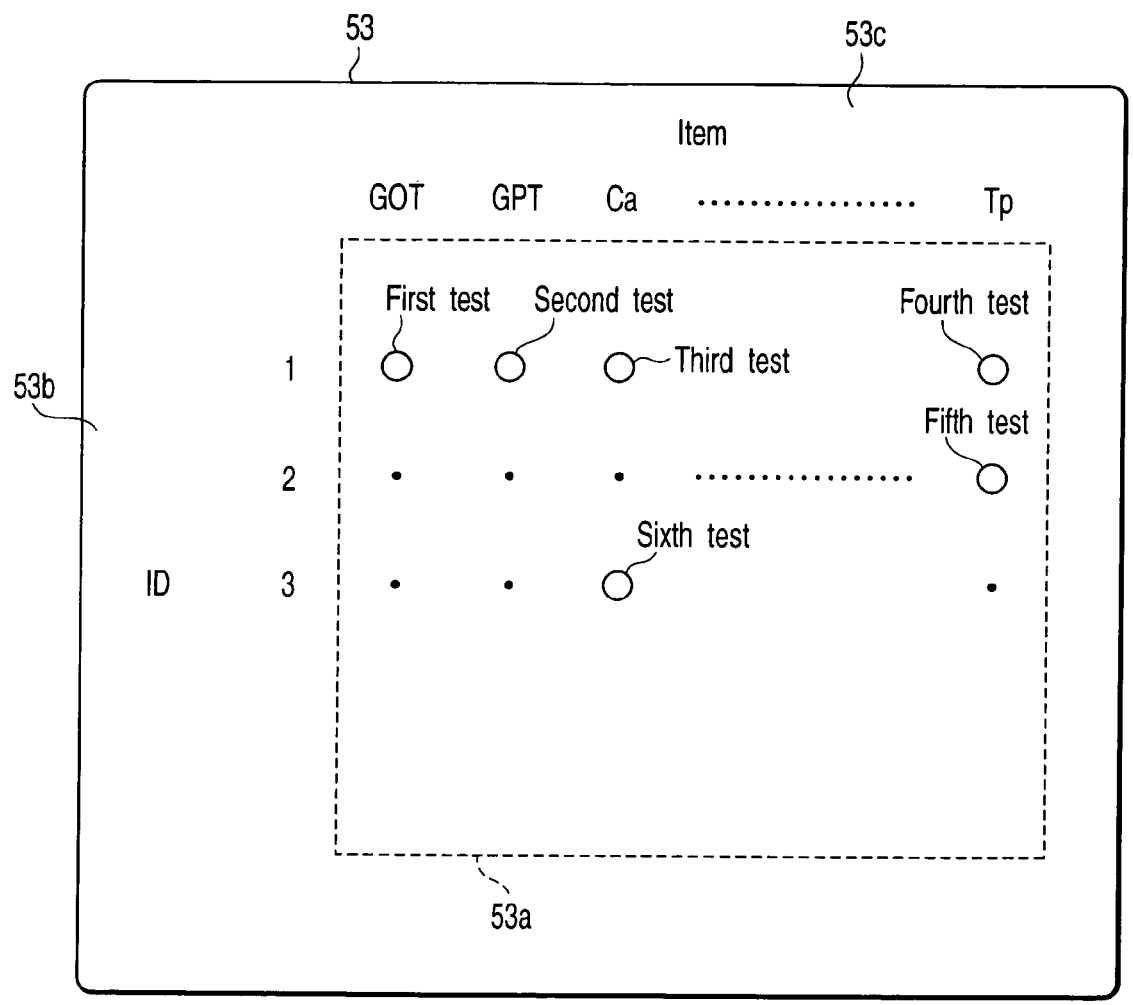
FIG. 7 is a view showing an example of a setting screen displayed on a display unit shown in FIG. 1 so as to set measurement items.

FIG. 7 is a view showing an example of a setting screen 53 displayed on the display unit 52 so as to set the measurement items.

The setting screen 53 includes a setting area 53*a*, and display columns 53*b* and 53*c*. The display column 53*b* displays patient IDs input by using an input screen for patient information. The display column 53*c* displays item names by abbreviations, respectively. The setting area 53*a* displays a setting status whether or not the analysis apparatus 100 measures the measurement items according to the item names displayed in the display column 53*c* for each patient ID displayed in the display column 53*b*. The setting area 53*a* displays, for instance, 'O' by association with combinations of the patient IDs and the item names set so as to be measured and displays '.' by association with combinations of the IDs and item names other than that combinations.

In the example in FIG. 7, the setting screen 53 displays '1', '2' and '3' as IDs in the display column 53*b*, and displays 'GOT', 'Ca', 'GPT' and 'TP' as item names in the display column 53*c*. The setting screen 53 displays the setting that the analysis apparatus 100 measures each measurement item of the item name 'GOT', item name 'Ca', item name 'GPT' and item name 'TI' in relation to the patient ID '1', measures the measurement item of the item name 'TP' in relation to the patient ID '2', and further, measures the measurement item of the item name 'Ca' in relation to the patient ID '3'.

The item names 'GOT' and 'Ca' are measured by using the reaction vessel 14*a*, with, for example, the analysis conditions relating to the first measurement channel set in advance. The item names 'GPT' and 'TP' are measured by using the reaction vessel 14*b* with, for example, the analysis conditions relating to the second measurement channel set in advance.

The setting information showing the setting status displayed on the setting screen 53 is stored in the internal storage circuit of the system control unit 70. The system control unit 70 controls the measurement for the test specimens on the basis of the setting information. The system control unit 70, for instance, controls so as to measure the test specimens in the order from the test specimen corresponding to the patient ID '1' at the up-most stage in the display column 53*b*, and in the order from the measurement item corresponding to the left side in the display column 53*c*.

In a step S1 in FIG. 6, the analysis apparatus 100 starts operations in response to the measurement start operation by the operation unit 60. The system control unit 70 instructs the measurement of each measurement item for each test specimen to the analysis control unit 30, the analysis data processing unit 40 and the output unit 50 on the basis of the setting information stored in the internal storage circuit.

In a step S2, the control unit 32 once moves each operation unit to home positions, respectively, in response to the instructions.

Figure 8:
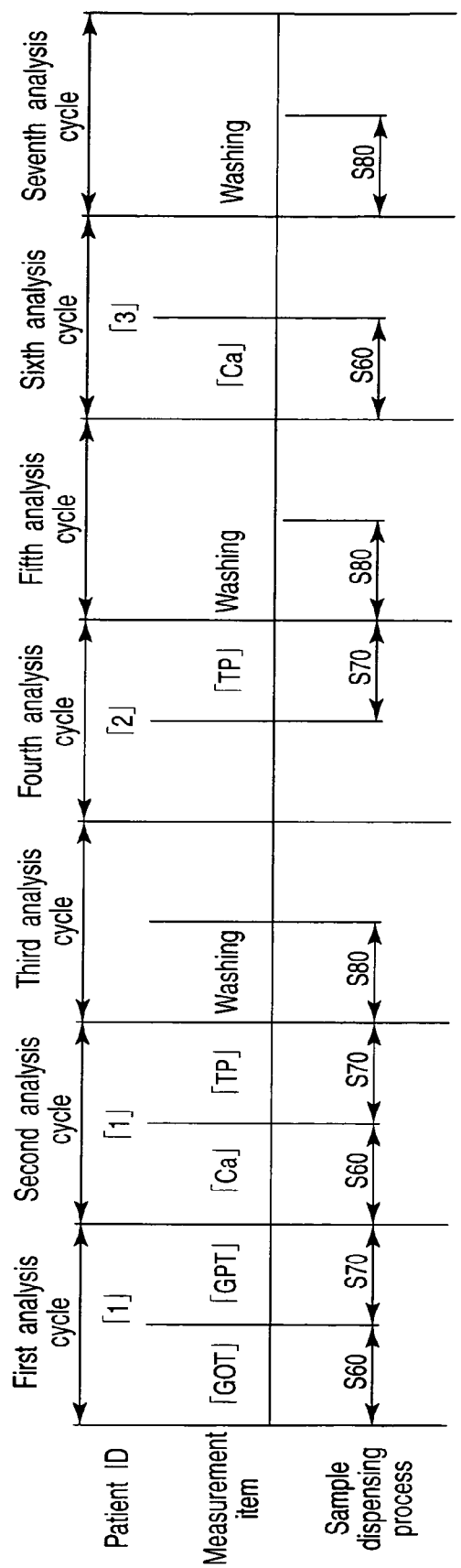
FIG. 8 is a view showing a correspondence of an example of an execution procedure of an analysis to execution procedures of the sample dispensing process and the probe washing process by the analysis apparatus shown in FIG. 1.

In a step S3, the measuring unit 20 executes the first process D60 and the second process S70. Here, the fist and second processes 60 and 70 dispense the test specimen to measure the measurement items of the item name 'GOT' and the test specimen to measure the measurement item of the item name 'GPT' in relation to the patient ID '1'. These processes S60 and S70 correspond to a first analysis cycle shown in FIG. 8.

In the first process S60 executed in the step S3, operations are performed sequentially as follows.

(1) The arm 4 rotates in the R1 direction in the rotation of the disk 15 to move the dispensing probe 5 from the washing position P4 to the aspiration position P1. The specimen vessel 1a with the test specimen related to the patient ID '1' held therein is positioned below the aspiration position P1 in advance. For instance, in the event that the specimen vessel 1a is set to the set position '1' at the rack 3 in FIG. 3, the rack 3 is moved so as to the set position '1' is positioned below the aspiration position P1 in advance. The arm 4 then lowers the dispensing probe 5 to the liquid surface detecting position of the test specimen held in the specimen vessel 1a positioned below the aspiration position P1 and stops.

(2) The pump 6 performs an operation to make the dispensing probe 5 aspirate the test specimen to be used for the measurement relating to the measurement item of the item name 'GOT' (corresponding to first test in FIG. 7).

The test specimen is aspirated and infused by the dispensing probe 5 via the pressure transferring medium such as water sealed in the flow path between the pump 6 and the dispensing probe 5. A dummy layer is formed between the test specimen of the set sample quantity and the transferring medium aspirated into the dispensing probe 5. The dummy layer is formed of the test specimen to be dispensed; however, the test specimen forming the dummy layer is not infused to the reaction vessels 14a and 14b. That is, the test specimen forming the dummy layer is not used for the measurement. The dummy layer prevents the test specimen from being diluted by the transferring medium. The dummy layer is formed by aspirating a fixed quantity of the test specimens for a dummy in preference to aspirating the test specimen in order to dispense it for the first measurement item for each test specimen. The test specimen forming the dummy layer is not infused from the dispensing probe 5 and used repeatedly in the dispensing probe 5 until the dispensing for all measurement items related to the same test specimen is completed.

(3) The arm 4 rises then rotates in the R2 direction. The arm 4 then lowers at the first infusion position P2 during the stoppage of the disk 15 to move the dispensing probe 5 into the reaction vessel 14a which is stopped below the first infusion position P2.

(4) The pump 6 infuses the test specimen relating to the measurement item of the item name 'GOT' from the dispensing probe 5 to the reaction vessel 14a.

(5) The arm 4 rises, rotates in the R1 direction, and then, moves the dispensing probe 5 to the washing position P4.

The second process S70 to dispense the test specimen of the measurement item of the item name 'GPT' in relation to the patient ID '1' is executed sequentially from the first process S60. The second process S70 conducts operations in succession as follows.

(1) The arm 4 rotates in the R1 direction to move the dispensing probe 5 from the washing position P4 to the aspiration position P1. The arm 4 lowers the dispensing probe 5 to the liquid surface detecting position of the test specimen held in the specimen vessel 1a positioned below the aspiration position P1, namely the specimen vessel 1a set to the set position '1' at the rack 3 and then stops.

(2) The pump 6 performs an operation to make the dispensing probe 5 aspirate the test specimen to be used for measurement relating the measurement item of the item name 'GPT' (corresponding to second test in FIG. 7).

(3) The arm 4 rises and rotates in the R2 direction. The Arm 4 then lowers from the second infusion position P3 to move the dispensing probe 5 into the reaction vessel 14b which is stopped below the second infusion position P3.

(4) The pump 6 makes the dispensing probe 5 infuse the test specimen related to the measurement item of the item name 'GPT' to the reaction vessel 14b.

(5) The arm 4 rises, rotates in the R1 direction, and then moves the dispensing probe 5 to the washing position P4.

In a step S4, the measuring unit 20 executes the sample dispensing process S50 so as to dispense the test specimen of the item names 'Ca' and 'TP' of the patient ID '1' like the forgoing manner. This process S50 is equivalent to a second analysis cycle shown in FIG. 8.

In a step S5, the measuring unit 20 executes the probe washing process S80 so as to wash off the test specimen of the patient ID '1' adherent to the dispensing probe 5. This step S80 corresponds to a third analysis cycle in FIG. 8.

The probe washing process S80 executed in a step S5 performs the following operations in succession.

(1) The arm 4 lowers until the tip of the dispensing probe 5 achieves the washing liquid infusion port below the washing position P4 and stops.

(2) The pump 6 washes the inner wall of the dispensing probe 5. The outer wall of the dispensing probe 5 is washed by the washing liquid from the infusion port.

Like this way, by washing the inner and outer walls of the dispensing probe 5 after completing the dispensing operation for the test specimen of the patient ID '1', the probe washing process S80 prevents the test specimen of the patient ID '1' from getting mixed with the test specimen of the patient ID '2' through the dispensing probe 5.

(3) The arm 4 rises up to stand by in preparation for dispensing the test specimen of the patient ID '2'.

In a step S6, the measuring unit 20 executes the second process S70 in order to dispense the test specimen for measuring the measurement item of the item name 'TP' in relation to the patient ID '2'. The second process S70 corresponds to a fourth cycle shown in FIG. 8.

In a step S7, the measuring unit 20 executes the probe washing process S80 so as to wash off the test specimen of the patient ID '2' adherent to the dispensing probe 5. This probe washing process S80 corresponds to a fifth analysis cycle shown in FIG. 8.

In a step 8, the measuring unit 20 executes the first process S60 so as to dispense the test specimen for measuring the measurement item of the item name 'Ca' in relation to the patient ID '3'. This first process S60 corresponds to a sixth analysis cycle in FIG. 8.

In a step S9, the measuring unit 20 executes the probe washing process S80 in order to wash off the test specimen of the patient ID '3' adherent to the dispensing probe 5. This washing process S80 corresponds to a seventh analysis cycle in FIG. 8.

In a step S10, the measuring unit 20 dispenses a first reagent. More specifically, the dispensing probes 12a and 12b infuse the first reagent aspirated from the reagent bottle 7a by the dispensing probes 12a and 12b into each reaction vessel 14a and 14b when the reaction vessels 14a and 14b with any one of the test specimens of the patient IDs '1' to '3' dispensed therein stops at the first or second infusion position for the first reagent.

In a step S11, the measuring unit 20 causes first stirring. Specifically, the test specimen and the first reagent dispensed in the reaction vessels 14a and 14b are stirred, respectively, by two stirring elements of the stirring unit 16a, when the reaction vessels 14a and 14b with any one of the test specimens of the patient IDs '1' to '3' and the first reagent dispensed therein stops below the two stirring positions of the stirring unit 16a.

In a step S12, the measuring unit 20 dispenses a second reagent. More specifically, the second reagent aspirated from the reagent bottle 7b by the dispensing probes 13a and 13b is infused to each reaction vessel 14a and 14b from the dispensing probes 13a and 13b when the reaction vessels 14a and 14b with the mixed liquid of any one of the patient IDs '1' to '3' and the first reagent held therein stops at the first or the second infusion positions for the second reagent. The second reagent dispensed here is one related to each measurement item of the item names 'GOT', 'GPT' and 'Ca'.

In a step S13, the measuring unit 20 performs second stirring. More specifically, the test specimen, the first reagent and the second reagent dispensed in the reaction vessels 14a and 14b are stirred, respectively, by two stirring elements of the stirring unit 16b, when the reaction vessels 14a and 14b with any one of the test specimens of the patient IDs '1' to '3', the first reagent and the second reagent dispensed therein stops below the two stirring positions of the stirring unit 16b.

In a step 14, the measuring unit 20 generates an analysis signal. Specifically, the photometry unit 17 emits light to the reaction vessels 14a and 14b to measure the absorbency of the set wavelengths from the light transmitted through the reaction vessels 14a and 14b when the reaction vessels 14a and 14b with the mixed liquid of the test specimen, the first and the second reagents, and the mixed liquid of the test specimen and the first reagent held therein. The photometry unit 17 generates analysis signals for each measurement item of each test specimen of the patient IDs '1' to '3' to output them to the analysis data processing unit 40.

In a step S15, the measuring unit 20 performs washing and drying of the reaction vessels. Specifically, the washing unit 18 aspirates the mixed liquid held in the reaction vessels 14a and 14b, and also washes and dries the inside thereof when the reaction vessels 14a and 14b with the mixed liquid of the test specimen, the first and second reagents and the mixed liquid of the test specimen and the first reagent held therein stops below the washing unit 18.

In a step S16, the analysis data processing unit 40 outputs the analysis data. More specifically, the calculation unit 41 generates the analysis data of each measurement item of each test specimen from the analysis signals output from the photometry unit 17 to store it in the storage unit 42, and also outputs it to the output unit 50.

In a step S17, the automatic analysis apparatus 100 terminates measurement operations.

The analysis apparatus 100 mentioned above shares one dispensing probe 5 to dispense the test specimen relating to each first and second measurement channel. As for the first measurement channel, the analysis apparatus 100 aspirates the test specimen to the dispensing probe 5 during the rotation of the disk 15 and infuses the test specimen to the reaction vessel 14a from the dispensing probe 5 immediately after the stoppage of the rotation of the disk 15. Successively, before the rotation of the disk 15 starts, as for the second measurement channel, the analysis apparatus 100 aspirates the test specimen to the dispensing probe 5 and infuses the test specimen to the reaction vessel 14a from the dispensing probe 5.

Thus, the analysis apparatus 100 is provided with only one system as a sample dispensing system composed of the arm 4, the dispensing probe 5, the pump 6, etc. and it can simplify its configuration and reduce a cost.

Since the sample dispensing system has only one dispensing probe, the amount in which any other specimen flows via the probe and mixes with the test specimen can be reduced. Practically, it is impossible to wash the dispensing probe completely clean. A small amount of tested specimen may inevitably remain in the probe even after the probe is washed. If left in the probe, the test specimen mixes with the next test specimen to be tested. The amount in which the tested specimen mixes with the next specimen is smaller than in the case where the test specimen is applied through two or more dispensing probes. Since the amount in which the test specimen mixes with the next test specimen, the next test specimen can be analyzed more accurately than otherwise.

The dispensing probe 5 aspirating only the test specimen of a quantity to dispense it to one reaction vessel, the analysis apparatus 100 can surely prevent the test specimen infused to the reaction vessel from being diluted by the pressure transferring medium in comparison to the conventional multiple item dispensing system. Thereby, the analysis apparatus 100 can dispense a test specimen with high purity, so that it can conduct an analysis with excellent precision.

In the conventional single item dispensing system, it is needed to insert two dispensing probes into a specimen vessel simultaneously. However, in the first embodiment, only one dispensing probe 5 is inserted into each specimen vessel 1a and 1b. Therefore, in the first embodiment, opening diameters of the specimen vessels 1a and 1b can be made smaller than those of the conventional dispensing system, and the liquid surface heights of the test specimens in the specimen vessels 1a and 1b can be maintained at defined heights by a small quantity of test specimens.

Furthermore, although dummies have to be aspirated to each of two dispensing probes in the conventional single item dispensing system, since the dummy has to be aspirated to only one dispensing probe 5, the quantity of the test specimens used for the dummy can be reduced.

Second Embodiment

A difference point between a second embodiment and the first embodiment is operation timing relating to a sample dispensing process. Therefore, a featured operation of the second embodiment will be described in detail and a description of its configuration will be omitted here.

Figure 9:
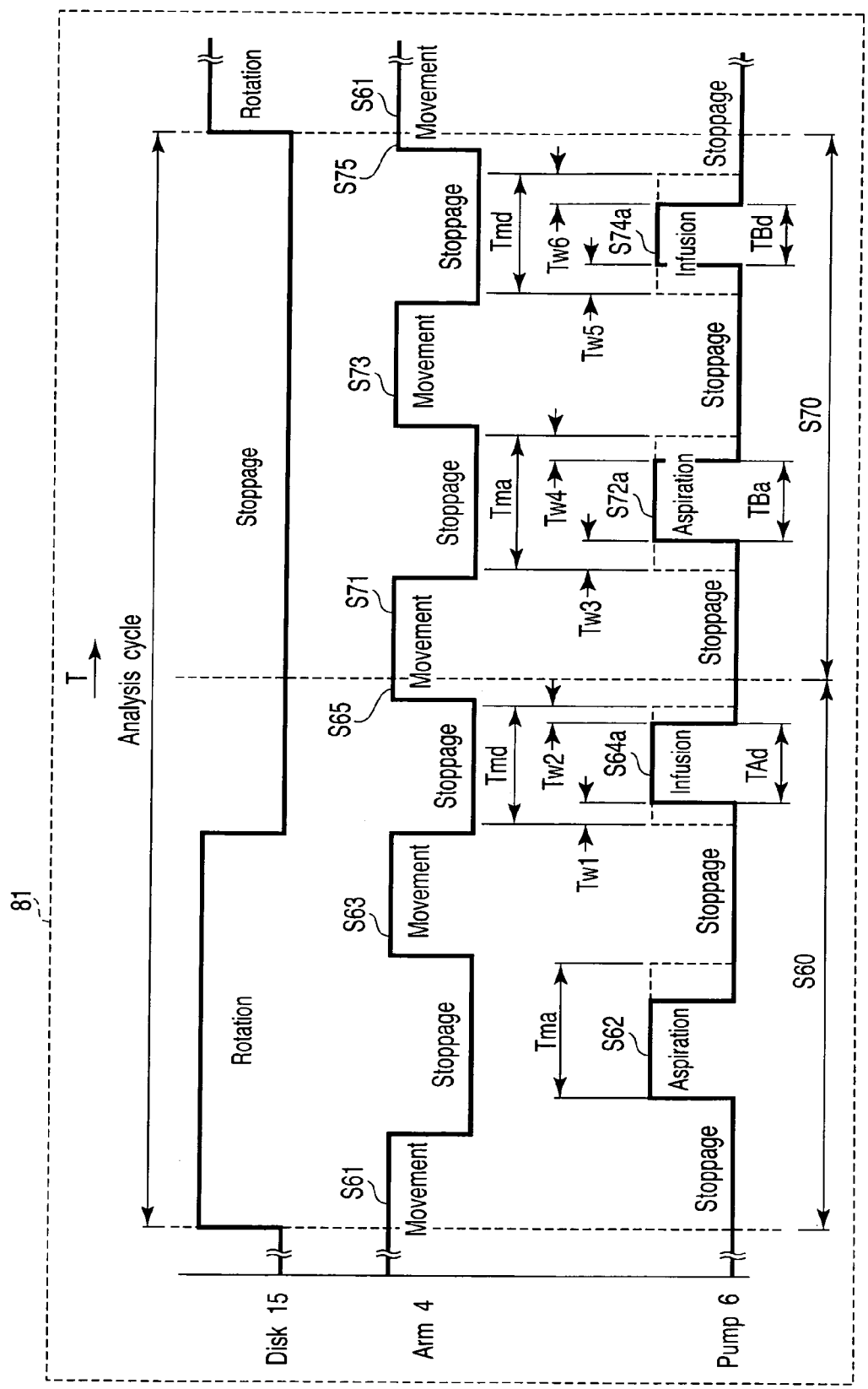
FIG. 9 is a timing chart showing timing of operations of each step of a sample dispensing process regarding a second embodiment of the present invention.

FIG. 9 is a timing chart 81 showing operation timing of each step in the sample dispensing process.

The timing chart 81 differs from the timing chart 80 in a point that the former enables varying the start and termination timing of the aspiration operation and the infusion operation of the pump 6 during the stoppage of the disk 15.

The timing chart 81 shows each operation start timing, operation time, and operation termination timing of the disk 15, the arm 4 and the pump 6 corresponding to steps S61, S62, S63, S64a and S65 to dispense the test specimen to the reaction vessel 14a, and corresponding to steps S71, S72a, S73, S74a and S75 to dispense the test specimen to the reaction vessel 14b.

The operation timing corresponding to the steps S64a, S72a and S74a in the timing chart 81 is made in a manner that the operation start and termination timing of each step are made variable within ranges of the operation timing corresponding to the steps S64, S72 and S74 in the timing chart 80.

Now, in the analysis conditions for the measurement items, there is some possibility only for some specific measurement items that sample qualities of the test specimen are set to each maximum quality and there is no possibility for other measurement items that the sample qualities of the test specimen are dispensed at each maximum quality. For instance, if it is presumed that a maximum sample quantity is 15 µL, averaged sample quantities set on the analysis conditions for many measurement items are 3 µL to 4 µL.

Therefore, in the second embodiment, when a measurement item with a sample quantity of a fine quantity of, for example, 1.5-4.0 µL easy to be reduced in dispensing precision is performed, the excess times shown in FIG. 5 are assigned to factors becoming below-mentioned errors of the dispensing precision.

Before executing the sample dispensing process S50, the system control unit 70 reads out the sample quantities set to the measurement items to be dispensed to the reaction vessels 14a and 14b in the sample dispensing process S50 to calculates times TAd, TBa and TBd, respectively, on the basis of the set sample quantities. The time TAd is a time required to infuse the test specimen to the reaction vessel 14a in the step S64a. The time TBa is a time needed to aspirate the test specimen for dispensing it to the reaction vessel 14b in the step S64a. The time TBd is a time required to infuse the test specimen to the reaction vessel 14b in the step S74.

Setting a time necessary for aspirating a maximum sample quantity to a time Tma, and setting a time necessary for infusing the maximum sample quantity to a time Tmd generate excess times indicated as (Tmd−TAd), (Tma−TBa) and (Tmd−TBd) in the steps S64a, S72a and S74a, respectively. These excess times are assigned to the error factors of the dispensing precision described below.

The excess times in the steps S64a, S72a and S74a are divided into times Tw1, Tw3 and Tw5 on a front side and times Tw2, Tw4 and Tw6 in a rear side.

The excess times Tw1 and Tw5 in the front side in the steps S64a and S74a are assigned, for instance, to an adjustment of a lowering speed of the arm 4, an adjustment of a waiting time until the pump 6 starts the infusion operation of the test specimen after the lowering operation of the arm 4, or the like.

The excess times Tw2 and Tw6 in the rear side in the steps S64a and S74a are assigned, for instance, to an adjustment of a lowering speed of the arm 4, an adjustment of a waiting time until the arm 16 starts the rising operation after the infusion operation of the pump 6, or the like.

The excess time Tw3 on the front side in the step S72a is assigned, for instance, to an adjustment of a lowering speed of the arm 4, and adjustment of a waiting time until the pump 6 starts the aspiration operation of the test specimen, or the like.

The excess time Tw4 on the rear side in the step S72a is assigned to an adjustment of a waiting time until the arm 16 starts the rising operation after the aspiration operation of the pump 6, an adjustment of the rising speed of the arm 4, and the like.

Thus, according to the second embodiment, the analysis apparatus 100 enables adjustments of operations causing the error factors of the dispensing precision, so that it can improve precision related to dispensing a slight amount of samples.

Third Embodiment

A different point between the third embodiment and the first embodiment is an operation timing relating to the sample dispensing process. Therefore, featured operations in the third embodiment will be described in detail and a description of its configuration will be omitted here.

FIG. 10 is a timing chart 82 showing operation in each step in the sample dispensing process.

The timing chart 82 differs from the timing chart 80 in a point that the former enables varying the start and termination timing of the movement of the arm 4 and of the aspiration operation and the infusion operation of the pump 6 during the stoppage of the disk 15.

The timing chart 82 shows each operation start timing, operation time, and operation termination timing of the disk 15, the arm 4 and the pump 6 corresponding to steps S61, S62, S63, S64b and S65b to dispense the test specimen to the reaction vessel 14a, and corresponding to steps S71b, S72b, S73b, S74b and S75b to dispense the test specimen to the reaction vessel 14b.

The operation termination timing corresponding to the steps S64b, operation start timing and termination timing corresponding to the step S72b and S74b, and operation start timing corresponding to the steps S65b, S73b and S75b are made variable on the timing chart 82. And except the excess times caused by operations corresponding to the steps S64b, S72b and S74b, the operations corresponding to the steps S64b, S65b and S71b to S75b are conducted successively.

It is presumed that the start timing of the infuse of the test specimen corresponding to the step S64b executed during the stoppage of the disk 15 is set to the timing after a fixed time t1 from the start timing of the rotation of the disk 15, and the time from the start timing of the infuse of the test specimen corresponding to the step S64b to the start timing of the next rotation of the disk 15 is set to a fixed maximum time Tmax.

The movement time of the dispensing probe 5 in response to the steps S65b and S71b is set to TBt. The movement time of the dispensing probe 5 corresponding to the step S75b is set to Th1. Further, the operation times of the infusion operations and the aspiration operations corresponding to the steps S64b, S72b and S74b are calculated from the system control unit 70 at every execution of the sample analysis process 50 and set to variable TAd, TBa and TBd for each measurement item.

The maximum time Tmax is expressed by a relational expression Tmax≥(TAd+TAt+TBa+TBt+TBd+TBt1). If the maximum time Tmax is equal to (TAd+TAt+TBa+TBt+TBd+TBt1), the timing chart 82 coincides with the timing chart 80.

Fourth Embodiment

A difference point between a fourth embodiment and the first embodiment is operation timing relating to the sample dispensing process. Therefore, a featured operation of the fourth embodiment will be described in detail and a description of its configuration will be omitted here.

Figure 11:
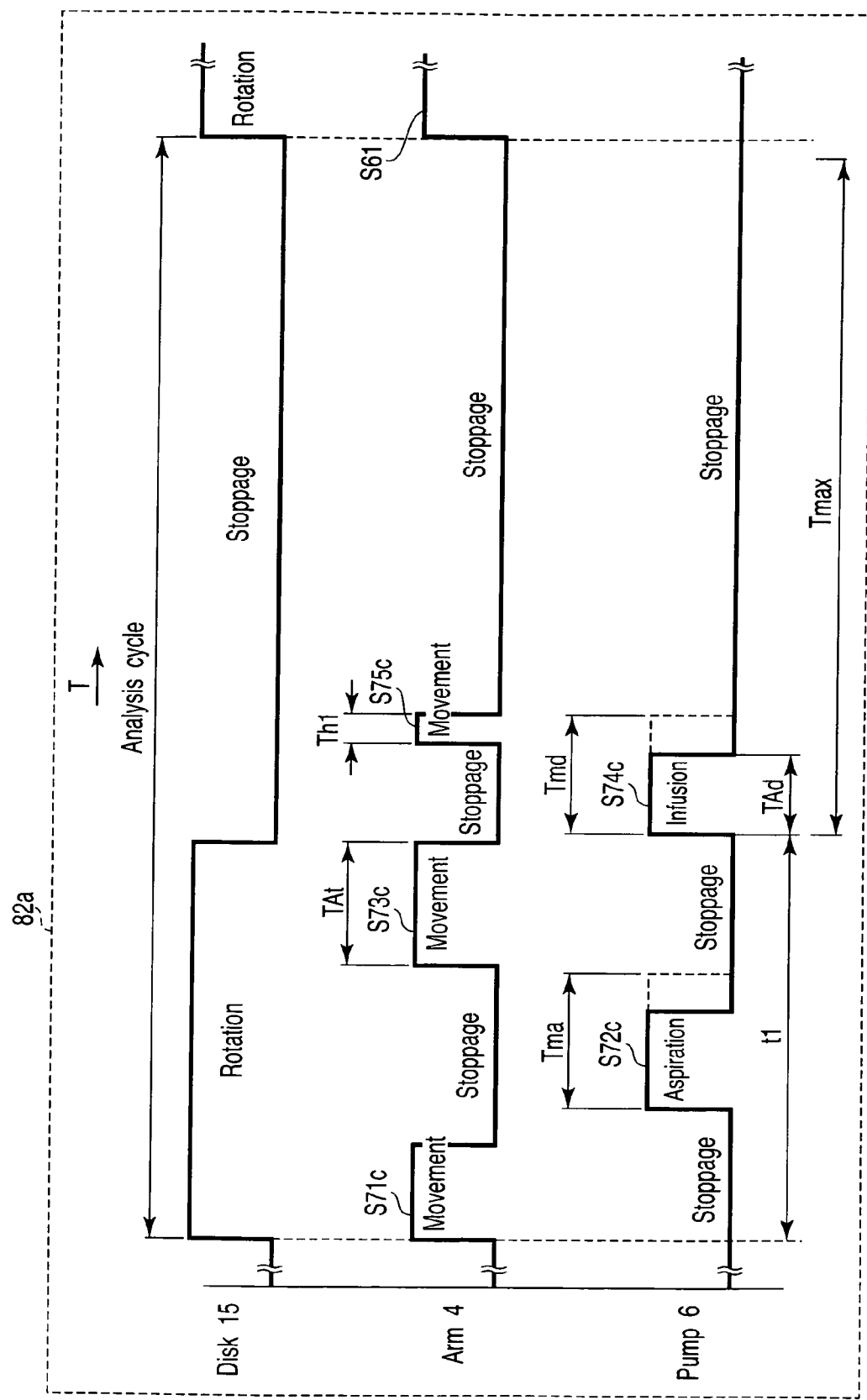
FIG. 11 is a timing chart in which a timing chart, by which dispensing of a test specimen in FIG. 10, is applied to the case where only dispensing of a test specimen to a reaction vessel 14$b$ in an analysis cycle is performed.

FIG. 11 is a timing chart 82a in which the timing chart 82 to dispense the test specimen in FIG. 10 is applied to the case where only the dispensing of the test specimen to the reaction vessel 14b is performed in the analysis cycle.

The timing chart 82a shows the operation start timing, the operation time and the operation termination timing of the disk 15, the arm 4 and the pump 6 corresponding to the steps S71c, S72c, S73c, S74c and S75c to dispense the test specimen to the reaction vessel 14b. Those timing almost coincide with the timing in the steps S61, S62, S63, S64b and S65b in FIG. 10.

Figure 12:
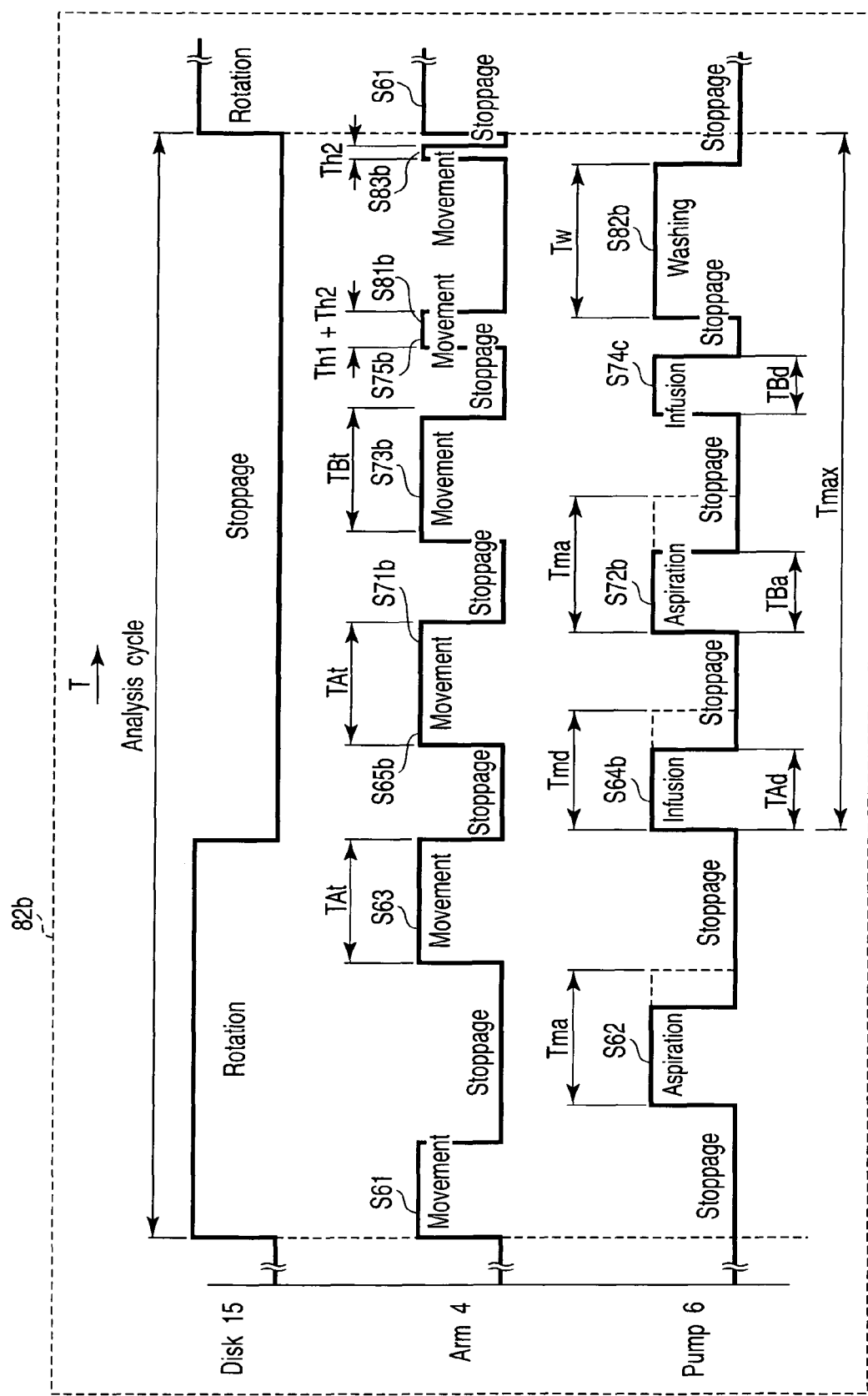
FIG. 12 is a flowchart showing timing of a washing operation performed after the dispensing operation of the test specimen in FIG. 10.

FIG. 12 is a timing chart 82b showing the timing of the washing operation performed after the dispensing operation for the test specimen in FIG. 10.

The timing chart 82b shows the timing of the movement corresponding to the step S81b, the washing operation corresponding to the step S82b and the movement corresponding to the step S83b continuously conducted after dispensing the test specimen to the reaction vessel 14a or 14b. And these timing is corresponding to the steps S81, S82 and S83 in the probe washing process S80, respectively.

If it is set that the operation times of the steps S81b, S82b and S83b are Th2, Tw and Th3, respectively, since the satisfaction of the expression: Tmax≥(TAd+TAt+TBa+TBt+TBd+Th1+Th2+Tw+Th3) makes it possible to conduct the washing operation during the stoppage of the disk 15, the timing chart 82b is executed. In the case of satisfaction of Tmax<(TAd+TAt+TBa+TBt+TBd+Th1+Th2+Tw+Th3), the steps S81, S82 and S83 in the timing chart 80 are executed.

As mentioned above, the start timing and termination timing of the aspiration operation and infusion operation, the start timing of the movement, and the start timing of the washing operation in the timing chart are made variable, and the movement and aspiration operations, infusion operation and washing operation are successively executed during the stoppage of the disk 15 except the excess time caused by the dispensing of the extremely small amount of samples. Thereby, according to the fourth embodiment, since the analysis apparatus can perform the dispensing of the test specimen to the reaction vessels 14a and 14b and the washing of the dispensing probe 5 within the analysis cycle, it can shorten the measurement time of measuring N pieces of test specimens to the measurement time of a (N−1) analysis cycle at a maximum.

The fourth embodiment may be modified in a variety of modifications as follows.

The present invention can be adapted to an automatic analysis apparatus with three or more measurement channels. In this case, the start and the termination timing of the aspiration operation and the infusion operation during the stoppage of the disk 15, and the start timing of the movement of the arm 4 are made variable. At every analysis cycle, the test specimen to be dispensed to the reaction vessel 14a during the rotation of the disk 15 is aspirated by the dispensing probe 5, and the infuse of the test specimen from the dispensing probe 5 to the reaction vessel 14a and the dispensing operations to the reaction vessel 14b and to the reaction vessels of each measurement channel after the third measurement channel are performed successively during the stoppage of the disk 15. Then, the analysis apparatus can obtain the same effect as that of the first embodiment, and in addition, it can process the test specimen at a high speed.

Further, the analysis apparatus may includes, for instance, a first to a fourth measurement channels; a first to a third reaction vessels and a first dispensing probe corresponding to the first to the third measurement channels; a second to a fourth reaction vessels and a second dispensing probe corresponding to the second and the fourth measurement channels; an arm to move the first and the second dispensing probes; a first and a second pumps connected to the first and the second dispensing probes, respectively; reagent dispensing system (dispensing probe, arm and pump), coming to eight in all, of two of which are each associated with first to fourth measurement channels, respectively; and a first and a second stirring units each having four stirring elements. The analysis apparatus aspirates the test specimen to be dispense into the first and the second reaction vessels by using the first and the second probes and pumps during the rotation of the disk 15, and infuses the test specimen from the first and second probes to the first and second reaction vessels from the first and second probes during the stoppage of the disk 15, and further, dispenses the test specimen to the third and fourth reaction vessels by using the first and the second probes and pumps.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An automatic analysis apparatus analyzing a test specimen held in a reaction vessel on a basis of a property of a mixed liquid of the test specimen and a reagent, comprising:
a moving unit which moves a plurality of reaction vessels then stops them at every analysis recycle;
a sample unit which aspirates the test specimen from a specimen vessel to infuse the test specimen to a first reaction vessel among the plurality of the reaction vessels stopped by the moving unit; and
a processor configured to control the sample unit so as to aspirate the test specimen during movements of the reaction vessels, infuse the test specimen to the first reaction vessel of the plurality of the reaction vessels after the reaction vessels are stopped, and repeatedly aspirate the test specimen and infuse the test specimen to one or more reaction vessels except the first reaction vessel among the plurality of the reaction vessels in a time period after the reaction vessels are stopped again and before the reaction vessels are moved.

2. The automatic analysis apparatus according to claim 1, wherein
the moving unit further comprises a disk holding a plurality of reaction vessel groups in a circular arrangement, each of the groups including at least two reaction vessels of the plurality of the reaction vessels, and
the moving unit rotates the disk by an angle to move from one reaction vessel group to a next reaction vessel group, so that the next reaction vessel group is in a dispensing position for the sample unit.

3. The automatic analysis apparatus according to claim 1, wherein
the sample unit further comprises a dispensing probe which aspirates the test specimen from the specimen vessel to dispense the test specimen.

4. The automatic analysis apparatus according to claim 1, wherein
the sample unit further comprises a dispensing probe which aspirates the test specimen from any of a plurality of specimen vessels in which a plurality of test specimens differing from one another are held, respectively, to infuse the aspirated test specimen; and
the automatic analysis apparatus further comprising a washing unit which washes the dispensing probe at every completion of dispensing of the same test specimen.

5. An automatic analysis apparatus analyzing a test specimen held in a reaction vessel on the basis of a property of a mixed liquid of the test specimen and a reagent, comprising:
a first moving unit which moves a plurality of reaction vessels then stops them at every analysis recycle;
an aspirating/infusing unit which aspirates the test specimen from a specimen vessel by a dispensing probe to infuse the test specimen;
a second moving unit which moves the dispensing probe; and
a processor configured to control the aspirating/infusing unit so as to aspirate the test specimen during movements of the plurality of the reaction vessels and after stopping the plurality of the reaction vessels, (i) controls the second moving unit so as to move the dispensing probe into a first reaction vessel among the plurality of the reaction vessels, (ii) controls the aspirating/infusing unit so as to infuse the test specimen into the specimen vessel, (iii) controls the second moving unit so as to move the dispensing probe to the specimen vessel, and (iv) controls the aspirating/infusing unit and the second moving unit so as to repeatedly aspirate the test specimen and infuse the test specimen to one or more reaction vessels except the first reaction vessel among the plurality of the reaction vessels during a time period where the plurality of reaction vessels are stopped again and before moving the plurality of reaction vessels.

6. The automatic analysis apparatus according to claim 5, wherein the moving unit further comprises a disk holding a plurality of reaction vessel groups in a circular arrangement, each of the groups including at least two reaction vessels of the plurality of the reaction vessels, and the moving unit rotates the disk by an angle to move from one reaction vessel group to a next reaction vessel group, so that the next reaction vessel group is in a dispensing position for the sample unit.

7. The automatic analysis apparatus according to claim 5, further comprising a washing unit which washes the dispensing probe at every completion of dispensing of the same test specimen.

8. The automatic analysis apparatus of claim 3, wherein the dispensing probe includes a plurality of specimen ejection positions.

* * * * *